United States Patent
Panse et al.

(10) Patent No.: US 11,532,130 B2
(45) Date of Patent: Dec. 20, 2022

(54) VIRTUAL AUGMENTATION OF ANATOMICAL MODELS

(71) Applicant: KONINKLIJKE PHILIPS N.V., Eindhoven (NL)

(72) Inventors: Ashish Panse, Burlington, MA (US); Molly Lara Flexman, Melrose, MA (US); Ayman Alalao, Cambridge, MA (US); Benoit Jean-Dominque Bertrand Maurice Mory, Medford, MA (US); Aleksandra Popovic, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 153 days.

(21) Appl. No.: 16/613,566

(22) PCT Filed: May 16, 2018

(86) PCT No.: PCT/EP2018/062828
§ 371 (c)(1),
(2) Date: Nov. 14, 2019

(87) PCT Pub. No.: WO2018/210980
PCT Pub. Date: Nov. 22, 2018

(65) Prior Publication Data
US 2021/0192845 A1 Jun. 24, 2021

Related U.S. Application Data

(60) Provisional application No. 62/506,928, filed on May 16, 2017.

(51) Int. Cl.
*G06T 19/00* (2011.01)
*A61B 34/10* (2016.01)
(Continued)

(52) U.S. Cl.
CPC ............ *G06T 19/006* (2013.01); *A61B 34/10* (2016.02); *G06F 3/033* (2013.01);
(Continued)

(58) Field of Classification Search
CPC ..... G06F 3/033; G06F 3/04815; A61B 34/10; A61B 2034/104; A61B 2034/105;
(Continued)

(56) References Cited

U.S. PATENT DOCUMENTS

2012/0280988 A1* 11/2012 Lampotang ........... G06T 19/006
345/419
2013/0331947 A1* 12/2013 Surma ................ A61B 17/1725
606/99

(Continued)

FOREIGN PATENT DOCUMENTS

| JP | 2007213407 A | 8/2007 |
| JP | 2016168078 A | 9/2016 |
| WO | 2012106706 A2 | 8/2012 |

OTHER PUBLICATIONS

Chen et al: "Development of a Surgical Navigation System Based on Augmented Reality Using an Optical See-Through Head-Mounted Display"; Journal of Biomedical Informatics, 55 (2015), p. 124-131.

(Continued)

*Primary Examiner* — Abderrahim Merouan

(57) ABSTRACT

A mixed reality device (30) employing a mixed reality display (40) for visualizing a virtual augmentation of a physical anatomical model, and a mixed reality controller (50) for controlling a visualization by the mixed reality display (40) of the virtual augmentation of the physical anatomical model including a mixed reality interaction between the physical anatomical model and a virtual anatomical model. The mixed reality controller (50) may employ a mixed reality registration module (51) for con- (Continued)

trolling a spatial registration between the physical anatomical model within a physical space and the virtual anatomical model within a virtual space, and a mixed reality interaction module for controlling the mixed reality interaction between the physical anatomical model and the virtual anatomical model based on the spatial registration between the physical anatomical model within the physical space and the virtual anatomical model within the virtual space.

19 Claims, 7 Drawing Sheets

(51) Int. Cl.
*G06F 3/033* (2013.01)
*G06F 3/04815* (2022.01)

(52) U.S. Cl.
CPC .... *G06F 3/04815* (2013.01); *A61B 2034/104* (2016.02); *A61B 2034/105* (2016.02); *G06T 2200/24* (2013.01); *G06T 2210/41* (2013.01); *G06T 2219/004* (2013.01)

(58) Field of Classification Search
CPC .............. G06T 19/006; G06T 2200/24; G06T 2210/41; G06T 2219/004
See application file for complete search history.

(56) References Cited

U.S. PATENT DOCUMENTS

| | | | |
|---|---|---|---|
| 2014/0071165 A1* | 3/2014 | Tuchschmid | G09B 23/30 345/633 |
| 2016/0314710 A1 | 10/2016 | Jare | |
| 2017/0092005 A1 | 3/2017 | Hasegawa | |
| 2017/0372640 A1* | 12/2017 | Lampotang | G09B 9/00 |

OTHER PUBLICATIONS

PCT/EP2018/062828, ISR & WO, dated Aug. 14, 2018, 18 Page Document.

Rolland et al: "Merging Augmented Reality and Anatomicaly Correct 3D Models in the Development of a Training Tool for Endotracheal Intubation"; IEEE, 2002, pp. 895-898.

Santhanam et al: "Real-Time Simulation and Visualization of Subject-Specific 3D Lung Dynamics"; Proceedings of the 19th IEEE Symposium on Computer-Based Medical Systems (CBMS'06), 6 Page Document.

Krevelen et al: "A Survey of Augmented Reality Technologies, Applications and Limitations"; The International Journal of Virtual Reality, 2010, vol. 9, pp. 1-20.

* cited by examiner

```
                        Medical procedure
                              70

┌─────────────────────────────────────────────────────────┐
    │              Virtual augmentation phase                 │
    │                         80                              │
    │  ┌──────────────┐  ┌──────────────┐  ┌──────────────┐   │
    │  │  Model/tool  │  │Physical space│  │ Mixed reality│   │
    │  │  acquisition │  │ virtual space│  │  interaction │   │
    │  │      81      │  │ registration │  │      83      │   │
    │  │              │  │      82      │  │              │   │
    │  └──────────────┘  └──────────────┘  └──────────────┘   │
    └─────────────────────────────────────────────────────────┘

┌─────────────────────────────────────────────────────────┐
    │              Procedure planning phase                   │
    │                         90                              │
    │  ┌──────────────┐  ┌──────────────┐  ┌──────────────┐   │
    │  │ Pre-operative│  │ Pre-operative│  │Intra-operative│  │
    │  │ consultation │  │path planning │  │path planning │   │
    │  │      91      │  │      92      │  │      93      │   │
    │  └──────────────┘  └──────────────┘  └──────────────┘   │
    └─────────────────────────────────────────────────────────┘

┌─────────────────────────────────────────────────────────┐
    │              Procedure execution phase                  │
    │                         100                             │
    │      ┌──────────────┐        ┌──────────────┐           │
    │      │Intra-operative│       │   Training   │           │
    │      │   feedback   │        │   feedback   │           │
    │      │     101      │        │     102      │           │
    │      └──────────────┘        └──────────────┘           │
    └─────────────────────────────────────────────────────────┘
```

FIG. 5

VIRTUAL AUGMENTATION OF ANATOMICAL MODELS

CROSS-REFERENCE TO PRIOR APPLICATIONS

This application is the U.S. National Phase application under 35 U.S.C. § 371 of International Application No. PCT/EP2018/062828, filed on May 16, 2018, which claims the benefit of U.S. Provisional Patent Application No. 62/506,928, filed on May 16, 2017. These applications are hereby incorporated by reference herein.

FIELD OF THE INVENTION

The present disclosure generally relates to various medical procedures (e.g., laparoscopic surgery, neurosurgery, spinal surgery, natural orifice transluminal surgery, cardiology, pulmonary/bronchoscopy surgery, biopsy, ablation, and diagnostic interventions). The present disclosure specifically relates to a fusion of an anatomical model and virtual information for various purposes, such as, for example, path planning, tool guidance, surgical training and patient consultation.

BACKGROUND OF THE INVENTION

Models of human anatomy have long been a part of surgical training, and also have a role in communicating with patients. Three-dimensional ("3D") printing has recently gained used in printing of anatomical models. These patient-specific models may help a surgical team prepare for a case and understand how to approach complex procedures and complex anatomies by facilitating a testing of specific therapies and a simulation of the therapies on model prior to the procedure. For example, a 3D printed model of an aortic valve may be used to plan and test out a trans-catheter valve deployment.

However, a 3D printing a patient specific anatomical model is often time consuming and an expensive process requiring expertise in multiple fields. First, a 3D imaging data set has to be segmented to generate a surface model of a patient anatomy of interest, and the surface model has to be edited so that it is compatible with the 3D printer technology. Second, current 3D printers may take significant time to print actual size 3D patient specific anatomical models of organs like the heart, vasculature, kidneys etc. In addition, a 3D patient specific anatomical model is not reusable for other patients.

Virtual models of a patient anatomy of interest may be generated using head-mounted mixed reality displays that also require the segmentation step, but don't require the aforementioned manufacturing hurdle of 3D printed patient specific anatomical models. Thus, virtual models are an appealing alternative to 3D printed patient specific anatomical models. However, there are still use cases where it is desirable to have a 3D printed patient specific anatomical models. For example, to see how that 3D printed patient specific anatomical models interacts with other objects such as therapeutic devices.

SUMMARY OF THE INVENTION

The present disclosure describes improvements to image guided therapies and diagnostic imaging as related to a medical procedure by providing a fusion of a physical anatomical model with additional virtual information.

A first embodiment of the inventions of the present disclosure is a mixed reality device employing a mixed reality display and a mixed reality controller. In operation, the mixed reality controller controls a visualization by the mixed reality display of a virtual augmentation of a physical anatomical model including a mixed reality interaction between the physical anatomical model and a virtual anatomical model.

The mixed reality interaction between the physical anatomical model and the virtual anatomical model as visualized by the mixed reality display may occur in a physical space or a virtual space.

The mixed reality interaction may involve an overlay of the virtual anatomical model onto the physical anatomical model whereby the physical anatomical model may serve as an anatomical joystick for manipulating the displayed view of the overlay of the virtual anatomical model onto the physical anatomical model within the physical space or the virtual space (e.g., a translation, a rotation and/or a pivoting of the physical anatomical model within the physical space serves to change the displayed view of the overlay of the virtual anatomical model of the physical anatomical model within the physical space or the virtual space).

A second embodiment of the inventions of the present disclosure is the mixed reality controller including a mixed reality registration module and a mixed reality interaction module. In operation, the mixed reality registration module controls a spatial registration of the physical anatomical model within the physical space and the virtual anatomical model within the virtual space, and the mixed reality interaction module controls the mixed reality interaction between the physical anatomical model and the virtual anatomical model based on the spatial registration of the models.

A third embodiment of the inventions of the present disclosure is a mixed reality method involving a mixed reality device controlling the spatial registration between the physical anatomical model within the physical space and the virtual anatomical model within the virtual space. The mixed reality method further involves the mixed reality device controlling a visualization of a mixed reality interaction between the physical anatomical model and the virtual anatomical model based on the spatial registration of the models.

For purposes of describing and claiming the inventions of the present disclosure:

(1) terms of the art of the present disclosure including, but not limited to, "mixed reality", "augmented reality", "augmented virtuality", "physical space" and "virtual space" are to be understood as known in the art of the present disclosure and exemplary described herein;

(2) the term "medical procedure" broadly encompasses all diagnostic, surgical and interventional procedures, as known in the art of the present disclosure and hereinafter conceived, for an imaging, a diagnosis and/or a treatment of a patient anatomy; (3) the term "anatomical model" broadly encompasses any type of physical or virtual representation of a patient anatomy suitable for a path planning, a tool guidance, a surgical training and/or a patient consultation as related to a medical procedure as exemplary described herein. The anatomical model, physical or virtual, may be patient-specific, such as, for example, via a manufacturing/computer generation of the anatomical model from an imaging of the patient anatomy or a delineation/computer generation of the anatomical model from the imaging of the patient anatomy for facilitating a selection or a morphing of a generic anatomical model, particularly manufactured from an anatomical atlas. Alternatively, the anatomical model may be non-patient-specific, such as, for example, a generic anatomical model manufactured/computer generated from an anatomical atlas or any type of object physically/virtually representative of the patient anatomy;

(4) the term "medical tool" broadly encompasses, as understood in the art of the present disclosure and hereinafter conceived, a tool, an instrument, a device or the like for physically or virtually conducting an imaging, a diagnosis and/or a treatment of a patient anatomy. Examples of a medical tool include, but are not limited to, robots, guidewires, catheters, scalpels, cauterizers, ablation devices, balloons, stents, endografts, atherectomy devices, clips, needles, forceps, k-wires and associated drivers, endoscopes, ultrasound probes, X-ray devices, awls, screwdrivers, osteotomes, chisels, mallets, curettes, clamps, forceps, periosteomes and j-needles.

(5) the term "mixed reality interaction" broadly encompasses, as known in the art of the present disclosure and exemplary described herein, a co-existence and interaction of physical and digital objects in real time within a merger of a physical space and a virtual space;

(6) the term "mixed reality device" broadly encompasses all devices incorporating a mixed reality controller within a mixed reality display or a linking of the mixed reality controller to the mixed reality display in accordance with the present disclosure;

(7) the term "mixed reality display" broadly encompasses all platforms as known in the art of the present disclosure and hereinafter conceived, for the implementation of a virtual argumentation of a physical anatomical model in support of a medical procedure. Examples of such mixed reality displays include, but are not limited to, head-mounted mixed reality displays (e.g., Google Glass, Hololens, Meta, Magic Leap and Vuzix) and tablets/smartphones/etc. functionally capable of visualizing a virtual argumentation of a physical anatomical model (e.g., an Apple iPad, an Apple iPhone, a Microsoft Surface and an Android tablet).

(8) the term "mixed realty controller" broadly encompasses all structural configurations, as understood in the art of the present disclosure and as exemplary described herein, of an application specific main board or an application specific integrated circuit as a component of a mixed reality device for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s), and network interface(s);

(9) the descriptive labels for term "controller" herein facilitates a distinction between controllers as described and claimed herein without specifying or implying any additional limitation to the term "controller";

(10) the term "module" broadly encompasses a module incorporated within or accessible by a controller consisting of an electronic circuit and/or an executable program (e.g., executable software stored on non-transitory computer readable medium(s) and/or firmware) for executing a specific application;

(11) the descriptive labels for term "module" herein facilitates a distinction between modules as described and claimed herein without specifying or implying any additional limitation to the term "module"; and

(12) the terms "signal", "data", and "command" broadly encompasses all forms of a detectable physical quantity or impulse (e.g., voltage, current, or magnetic field strength) as understood in the art of the present disclosure and as exemplary described herein for communicating information and/or instructions in support of applying various inventive principles of the present disclosure as subsequently described herein. Signal/data/command communication between components of the present disclosure may involve any communication method, as known in the art of the present disclosure and hereinafter conceived, including, but not limited to, data/command transmission/reception over any type of wired or wireless medium/datalink and a reading of data/command uploaded to a computer-usable/computer readable storage medium.

The foregoing embodiments and other embodiments of the inventions of the present disclosure as well as various features and advantages of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of present disclosure being defined by the appended claims and equivalents thereof.

BRIEF DESCRIPTION OF THE DRAWINGS

FIG. 5 illustrates a block diagram of an exemplary embodiment of a virtual augmentation based medical procedure in accordance with the inventive principles of the present disclosure.

DETAILED DESCRIPTION OF THE PREFERRED EMBODIMENTS

Figure 1A:
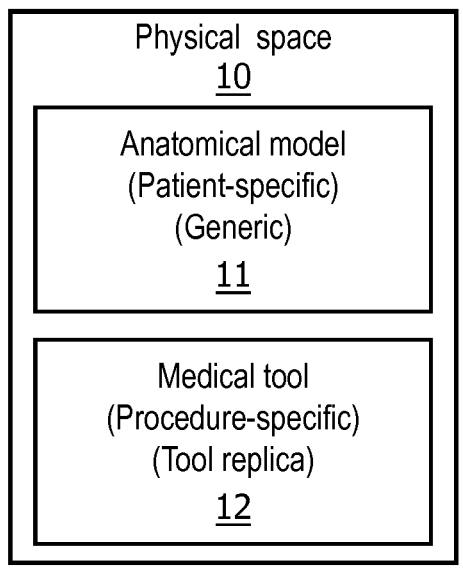
FIG. 1A illustrates various embodiments of a physical model in accordance with the inventive principles of the present disclosure.
Figure 1B:
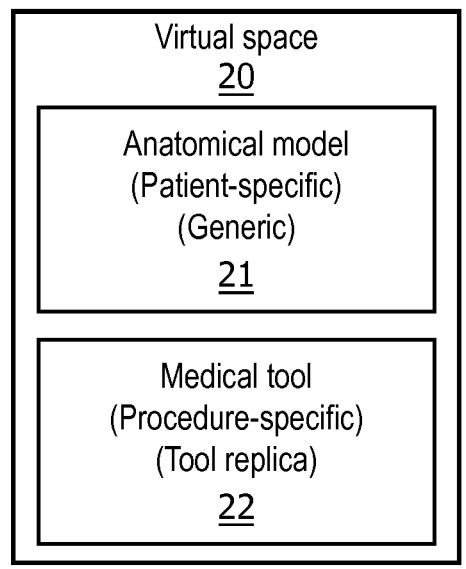
FIG. 1B illustrates various embodiments of a virtual model in accordance with the inventive principles of the present disclosure.

The present disclosure is premised on a merger of a physical space 10 of FIG. 1A and a virtual space 20 of FIG.

1B to facilitate a virtual augmentation of a physical anatomical model 11 of FIG. 1A in support of executing a subject medical procedure.

Referring to FIG. 1A, physical space 10 represents any real world space containing one or more physical anatomical models 11 and/or one or more physical medical tools 12 as related to various aspects of the subject medical procedure. Examples of physical space 10 include, but are not limited to, an operating room, a surgical planning facility, a surgical training classroom and a patient waiting room.

In practice, a physical anatomical model 11 may have any form suitable for the subject medical procedure.

In a first embodiment, a physical anatomical model 11 is patient-specific, such as, for example, via a manufacturing of the physical anatomical model from an imaging of the patient anatomy or a delineation of the physical anatomical model from the imaging of the patient anatomy for facilitating a selection or a morphing of a generic physical anatomical model, particularly manufactured from an anatomical atlas.

In a second embodiment, a physical anatomical model 11 is a generic anatomical model manufactured from an anatomical atlas or any type of object serving as a replica of the patient anatomy.

In practice, a physical anatomical model 11 may be hand-held, robot-held or otherwise supported by a platform.

In practice, a physical medial tool 12 may have any form suitable for the subject medical procedure. More particularly, a physical medical tool 12 may be utilized to test for a sizing, a positioning, an orientation, etc. of physical medical tool 12 relative to physical anatomical model 11 to facilitate the subject medical procedure.

In a first embodiment, a physical medical tool 12 is procedure-specific, such as, for example, a stent for performing a neurovascular stenting of an aneurism.

In a second embodiment, a physical medical tool 12 may be a tool replica, which is a physical representation of a procedure-specific medical tool that is structurally equivalent and/or functionally equivalent to a physical operation of the procedure-specific medical tool. Examples of a tool replica include, but are not limited to, a model of a physical medical tool 12, a laser pointer and an optical projector.

In practice, a physical medical tool 12 may be hand-held, robot-held or otherwise supported by a platform.

Virtual space 20 is a computer-generated, three-dimensional ("3D") representation of a physical space 10 containing one or more virtual anatomical models 21 and/or one or more virtual medical tools 22.

In practice, a merger of a particular physical space 10 and virtual space 20 may involve virtual space 20 representing the subject physical space 10 (e.g., both physical space 10 and virtual space 20 encompass the same operating room) or may involve virtual space 20 representing a different physical space 10 (e.g., physical space 10 being a surgical training facility and virtual space 20 representing an operating room, or vice-versa).

In practice, a virtual anatomical model 21 is a computer-generated 3D representation of a portion and an entirety of a patient anatomy represented by a physical anatomical model 21, or is computer-generated 3D representation of a different patient anatomy associated with the patient anatomy represented by a physical anatomical model 21 (e.g., adjacent anatomical regions, soft tissue, bones, vessels, skins, etc.).

Also in practice, a virtual anatomical model 21 may provide static anatomical/non-anatomical information and/or dynamic anatomical/non-anatomical information (e.g., a beating heart, electrical pathways, fluid flow, functional information fMRI, etc.)

In a first embodiment, a virtual anatomical model 21 is patient-specific, such as, for example, via a computer generation of the virtual anatomical model from an imaging of the patient anatomy or a computer generation of a morphed generic anatomical model in view of the imaging of the patient anatomy.

In a second embodiment, a virtual anatomical model 21 is a computer generation of a generic anatomical model manufactured from an anatomical atlas of the patient anatomy or any type of object serving as a replica of the patient anatomy.

In practice, a virtual medical tool 22 is a computer-generated 3D representation of a portion or an entirety of a physical medical tool 12 suitable for the particular medical procedure.

To facilitate an understanding of the present disclosure, the following description of FIGS. 2-5 teaches basic inventive principles of the present disclosure for executing a virtual augmentation of a physical anatomical model 11. From this description, those having ordinary skill in the art will appreciate how to apply the inventive principles of the present disclosure to making and using numerous and varied embodiments of devices, controllers and methods for executing a virtual augmentation of a physical anatomical model 11.

Figure 2A:
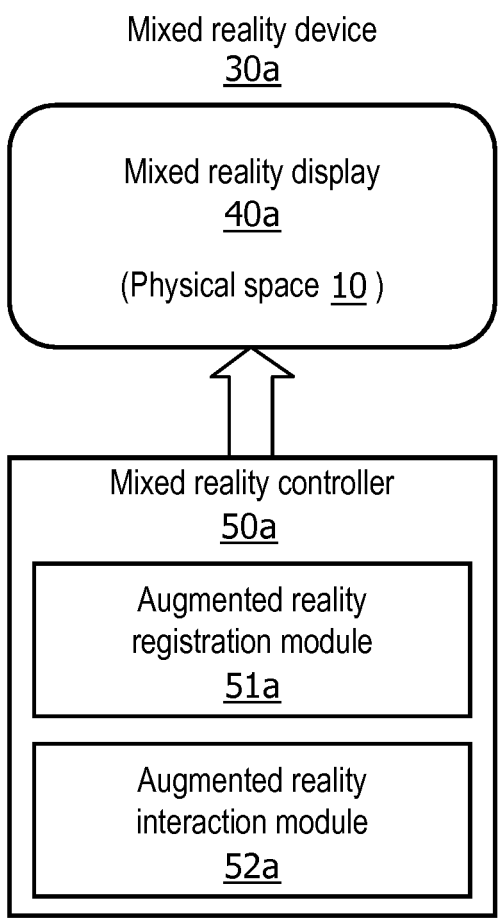
FIG. 2A illustrates an exemplary embodiment of a mixed reality device for an augmented reality in accordance with the inventive principles of the present disclosure.
Figure 2B:
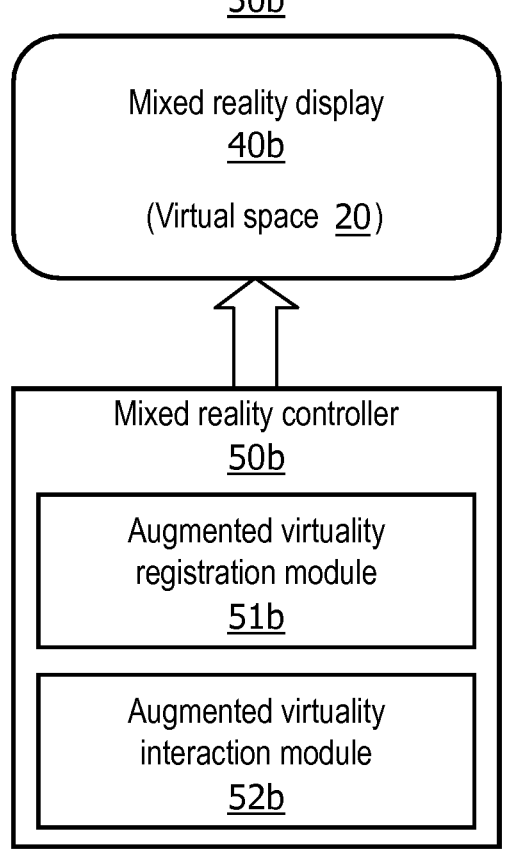
FIG. 2B illustrates an exemplary embodiment of a mixed reality device for an augmented virtuality in accordance with the inventive principles of the present disclosure.

FIG. 2A illustrates a mixed reality device 30a for performing an augmented reality based virtual augmentation of a physical anatomical model 11 within a physical space 10, and FIG. 2B illustrates a mixed reality device 30a for performing an augmented virtuality based virtual augmentation of a physical anatomical model 11 within a virtual space 20.

Referring to FIG. 2A, mixed reality display 30a employs a mixed reality display 40a (e.g., a head-mounted display, a tablet, a smartphone, etc.) and a mixed realty controller 50a.

In practice, mixed reality controller 50a may be installed within or linked to mixed reality display 30a.

Mixed reality display 40a provides for a visualization of a virtual augmentation of a physical anatomical model 11 within physical space 10 as will be further exemplary described herein.

In practice, a mixed reality device 40a will incorporate sensing technology, as known in the art of the present disclosure or hereinafter conceived, for tracking a pose of physical anatomical model 11 within physical space 10. Examples of such sensing technology includes, but is not limited to, cameras, depth sensors, markers attached/build into physical anatomical model 11 and inertial measurement units attached/integrated into physical anatomical model 11.

Mixed reality controller 50a provides for a control of the visualization by mixed reality display 40a of a virtual augmentation of a physical anatomical model 11 within physical space 10 including a mixed reality interaction between a physical anatomical model 11 and a virtual anatomical model 21.

In practice, mixed reality controller 50a exchanges sensing data with display controller(s) of mixed reality device 40a informative of the pose of physical anatomical model 11 within physical space 10 to thereby provide commands to the display controller(s) of mixed reality device 40a for the mixed reality interaction between the physical anatomical model 11 and the virtual anatomical model 21.

Alternatively in practice, mixed reality controller 50a is integrated with the display controller(s) of mixed reality device 40a to thereby command the mixed reality interaction between the physical anatomical model 11 and the virtual anatomical model 21.

In one embodiment, mixed reality controller 50a employs a mixed reality registration module in the form of an augmented reality registration module 51a and a mixed reality interaction module in the form of an augmented reality interaction module 52a. Augmented reality registration module 51a and augmented reality interaction module 52a execute a virtual augmentation method as represented by a flowchart 60 shown in FIG. 3.

Figure 3:
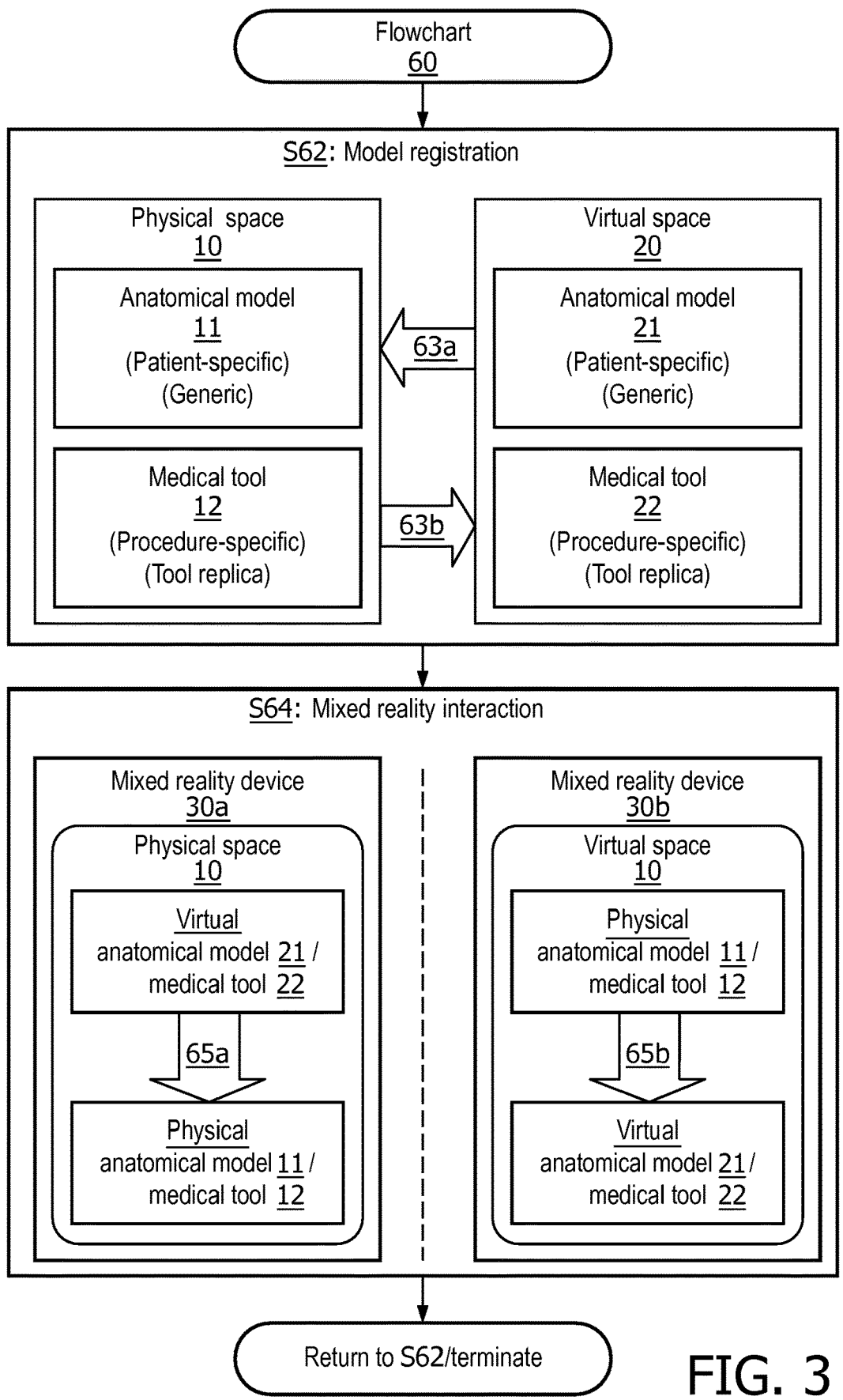
FIG. 3 illustrates a flowchart representative of an exemplary embodiment of a method for a virtual augmentation of a physical anatomical model in accordance with the inventive principles of the present disclosure.

Referring to FIG. 3, a stage S62 of flowchart 60 encompasses augmented reality registration module 51a controlling a spatial registration 63a of a virtual anatomical model 21 within virtual space 20 to a physical anatomical model 11 within a physical space 10.

In practice, augmented reality registration module 51a may execute any type of spatial registration suitable for the subject medical procedure, such as, for example, object feature detection, marker detection, point based registration and external tracking methods (e.g., optical tracking, electromagnetic tracking, etc.).

A stage S62 of flowchart 60 encompasses augmented reality interaction module 52a controlling a mixed reality interaction 65a between the spatially registered physical anatomical model 11 and virtual anatomical model 21 within physical space 10.

In practice, augmented reality interaction module 52a provides one more aspects of a mixed reality interaction 65a between the spatially registered physical anatomical model 11 and virtual anatomical model 21 within physical space 10.

In a first embodiment, an augmented reality interaction 65a between a physical anatomical model 11 and a virtual anatomical model 21 includes a virtual interactive overlay of the virtual anatomical model 21 onto the physical anatomical model 11 within physical space 10. With this embodiment, a translation, a rotation and/or a pivoting of the physical anatomical model 11 as sensed by mixed reality display 40a serves to change the displayed pose of the overlay of the virtual anatomical model 21 of the physical anatomical model 11.

In a second embodiment, an augmented reality interaction 65a between a physical anatomical model 11 and a virtual anatomical model 21 includes a virtual alteration of the physical anatomical model 11 via a virtual anatomical model 21, particularly based on surgical and/or training alterations to the corresponding patient anatomy.

Figure 4A:
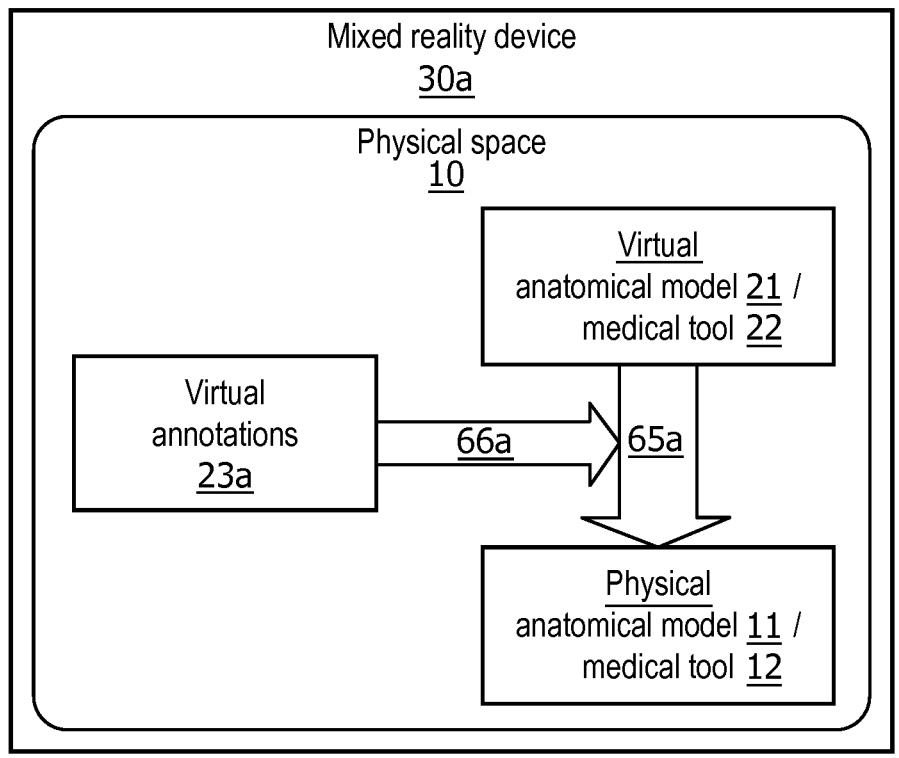
FIG. 4A illustrates an exemplary embodiment of a mixed reality display for an annotated augmented reality in accordance with the inventive principles of the present disclosure.

Still referring to FIG. 3, stage S64 of flowchart 60 may further encompass augmented reality interaction module 52a controlling a virtual annotation of the augmented reality interaction between a physical anatomical model 11 and a virtual anatomical model 21 (e.g., a delineation of landmarks, planned paths, notes, etc.). For example, FIG. 4A illustrates a delineation 66a of virtual annotations 23a of the augmented reality interaction between a physical anatomical model 11 and a virtual anatomical model 21.

Also in practice, mixed reality controller 50a may also provide for a control of a virtual augmentation of a physical anatomical model 11 within physical space 10 further including a mixed reality interaction (1) between a physical anatomical model 11 and a virtual medical tool 22, (2) between a physical medical tool 12 and virtual anatomical model 21, and/or (3) between a physical medical tool 12 and a virtual medical tool 22.

Referring to FIG. 2B, mixed reality display 30b employs a mixed reality display 40b (e.g., a head-mounted display, a tablet, a smartphone, etc.) and a mixed realty controller 50b.

In practice, mixed reality controller 50b may be installed within or linked to mixed reality display 30b.

Mixed reality display 40b provides for a visualization of a virtual augmentation of a physical anatomical model 11 within virtual space 20 as will be further exemplary described herein.

In practice, a mixed reality device 40b will incorporate sensing technology, as known in the art of the present disclosure or hereinafter conceived, for tracking a pose of physical anatomical model 11 within physical space 10. Examples of such sensing technology includes, but is not limited to, cameras, depth sensors, markers attached/build into physical anatomical model 11 and inertial measurement units attached/integrated into physical anatomical model 11.

Mixed reality controller 50b provides for a control of the visualization by mixed reality display 40b of a virtual augmentation of a physical anatomical model 11 within virtual space 20 including a mixed reality interaction between a physical anatomical model 11 and a virtual anatomical model 21.

In practice, mixed reality controller 50b exchanges sensing data with display controller(s) of mixed reality device 40b informative of the pose of physical anatomical model 11 within physical space 10 to thereby provide commands to the display controller(s) of mixed reality device 40b for the mixed reality interaction between the physical anatomical model 11 and the virtual anatomical model 21.

Alternatively in practice, mixed reality controller 50b is integrated with the display controller(s) of mixed reality device 40b to thereby command the mixed reality interaction between the physical anatomical model 11 and the virtual anatomical model 21.

In one embodiment, mixed reality controller 50b employs a mixed reality registration module in the form of an augmented virtuality registration module 51b and a mixed reality interaction module in the form of an augmented virtuality interaction module 52b. Augmented virtuality registration module 51b and augmented virtuality interaction module 52b execute a virtual augmentation method as represented by flowchart 60 shown in FIG. 3.

Referring to FIG. 3, a stage S62 of flowchart 60 encompasses augmented virtuality registration module 51b controlling a spatial registration 63b of a physical anatomical model 11 within a physical space 10 to a virtual anatomical model 21 within virtual space 20.

In practice, augmented virtuality registration module 51b may execute any type of spatial registration suitable for the subject medical procedure, such as, for example, object feature detection, marker detection, point based registration and external tracking methods (e.g., optical tracking, electromagnetic tracking, etc.).

A stage S62 of flowchart 60 encompasses augmented virtuality interaction module 52b controlling a mixed reality interaction 65b between the spatially registered physical anatomical model 11 and virtual anatomical model 21 within virtual space 20.

In practice, augmented virtuality interaction module 52b provides one more aspects of a mixed reality interaction 65b between the spatially registered physical anatomical model 11 and virtual anatomical model 21 within virtual space 20.

In a first embodiment, an augmented virtuality interaction 65b between a physical anatomical model 11 and a virtual anatomical model 21 includes a virtual interactive overlay of the virtual anatomical model 21 onto the physical anatomical model 11 within virtual space 20. With this embodiment, a translation, a rotation and/or a pivoting of the physical anatomical model 11 as sensed by mixed reality display 40b serves to change the displayed pose of the overlay of the virtual anatomical model 21 of the physical anatomical model 11.

In a second embodiment, an augmented virtuality interaction 65b between a physical anatomical model 11 and a virtual anatomical model 21 includes a virtual alteration of the physical anatomical model 11 via a virtual anatomical model 21, particularly based on surgical and/or training alterations to the corresponding patient anatomy.

Figure 4B:
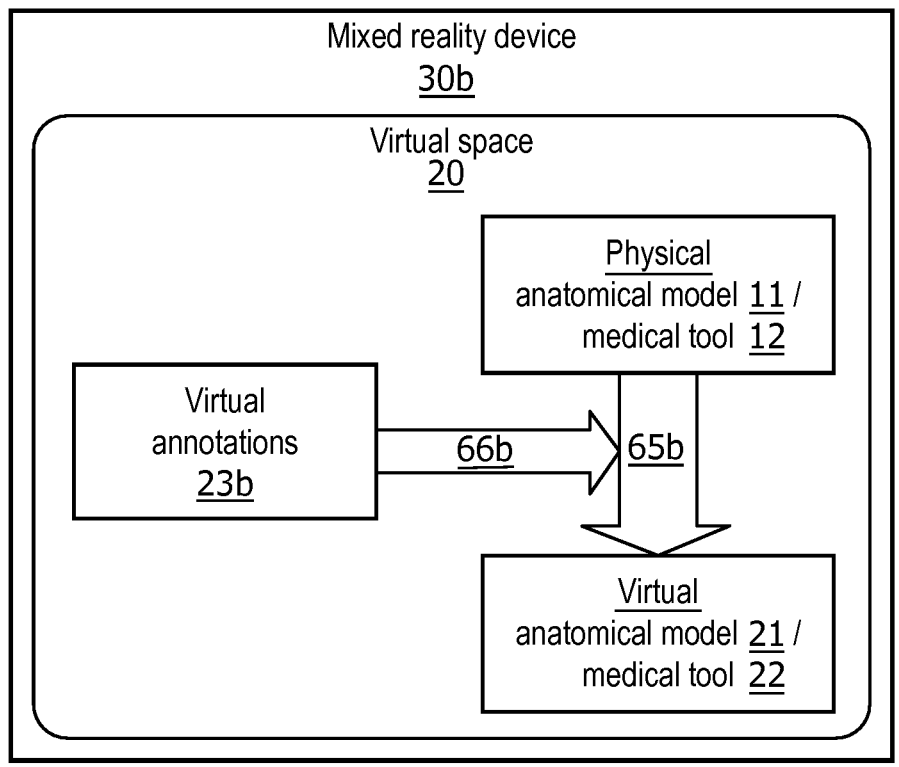
FIG. 4B illustrates an exemplary embodiment of a mixed reality display for an annotated augmented virtuality in accordance with the inventive principles of the present disclosure.

Still referring to FIG. 3, stage S64 of flowchart 60 may further encompass augmented virtuality interaction module 52b controlling a virtual annotation of the augmented virtuality interaction between a physical anatomical model 11 and a virtual anatomical model 21 (e.g., a delineation of landmarks, planned paths, notes, etc.). For example, FIG. 4B illustrates a delineation 66b of virtual annotations 23b of the augmented virtuality interaction between a physical anatomical model 11 and a virtual anatomical model 21.

Also in practice, mixed reality controller 50b may also provide for a control of a virtual augmentation of a physical anatomical model 11 within virtual space 20 further including a mixed reality interaction (1) between a physical anatomical model 11 and a virtual medical tool 22, (2) between a physical medical tool 12 and virtual anatomical model 21, and/or (3) between a physical medical tool 12 and a virtual medical tool 22.

FIG. 5 illustrates a virtual augmentation based medical procedure 70 of the present disclosure implementing a virtual augmentation phase 80, a procedure planning phase 90 and a procedure execution phase 100 for conducting a subject medical procedure.

Virtual augmentation phase 80 generally provides for the virtual augmentation of a physical anatomical model 11.

In one embodiment as shown, virtual augmentation phase 80 involves a model/tool acquisition 81 for the manufacturing, computer generation and/or otherwise acquisition of all models and tools necessary for the subject medical procedure.

Virtual augmentation phase 80 further involves physical space-virtual space registration 82 as previously described herein, and a mixed reality interaction 83 between models and/or tools as previously described herein.

Procedure planning phase 90 generally provides for a planning of the subject medical procedure.

In one embodiment, procedure planning phase 90 may involve a pre-operative consultation 91 between a physician and a patient (or third party) whereby the physician operates the physical anatomical model 11 as a joystick to manipulate a displayed pose of overlay of the virtual anatomical model 12 onto the physical anatomical model 11 to thereby facilitate an explanation of the subject medical procedure.

Procedure planning phase 90 may further involve a pre-operative path planning 92 and an intra-operative path planning 93 whereby a planned path may be pre-operatively and/or intra-operatively annotated relative to the overlay of the virtual anatomical model 12 onto the physical anatomical model 11.

Procedure execution phase 100 generally provides for a feedback from an execution of the subject medical procedure.

In one embodiment, procedure execution phase 100 may involve an intra-operative feedback 101 whereby a virtual anatomical model 21 may be altered to reflect any physical surgical alterations to the subject patient anatomy.

Procedure execution phase 100 may further involve training feedback 102 whereby a virtual anatomical model 21 may be altered to reflect any virtual surgical alternations to a physical anatomical model 21 and/or a virtual anatomical model 22.

Figure 6:
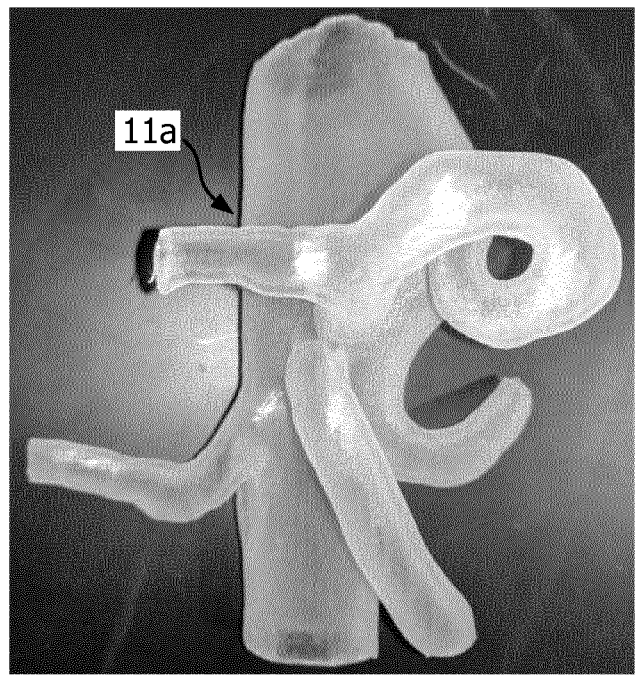
FIG. 6 illustrates an exemplary embodiment of a 3D printed physical model of an aneurysm as known in the prior art.
Figure 7A:
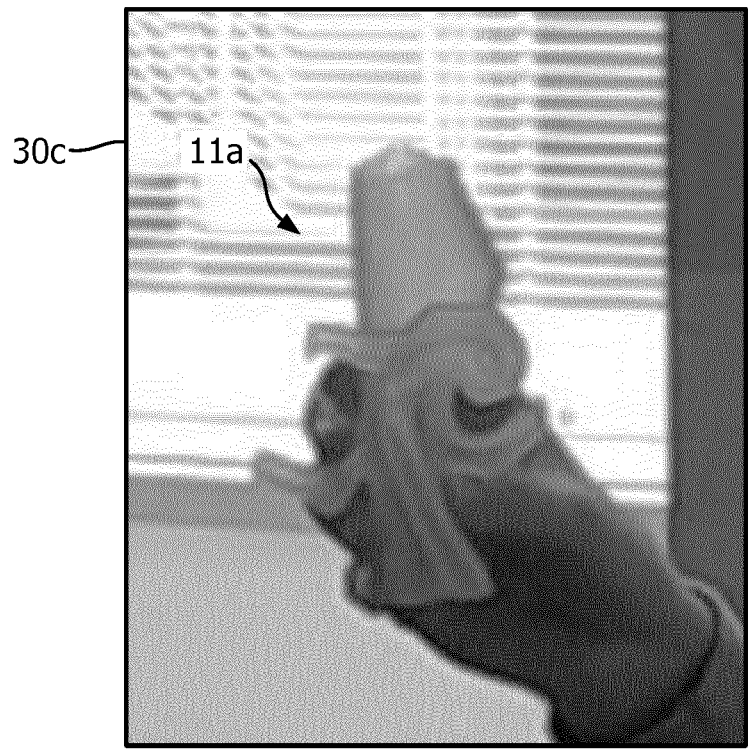
FIGS. 7A-7C illustrates an exemplary virtual augmentation of the 3D printed physical model of an aneurysm of FIG. 6 in accordance with the inventive principles of the present disclosure.
Figure 7B:
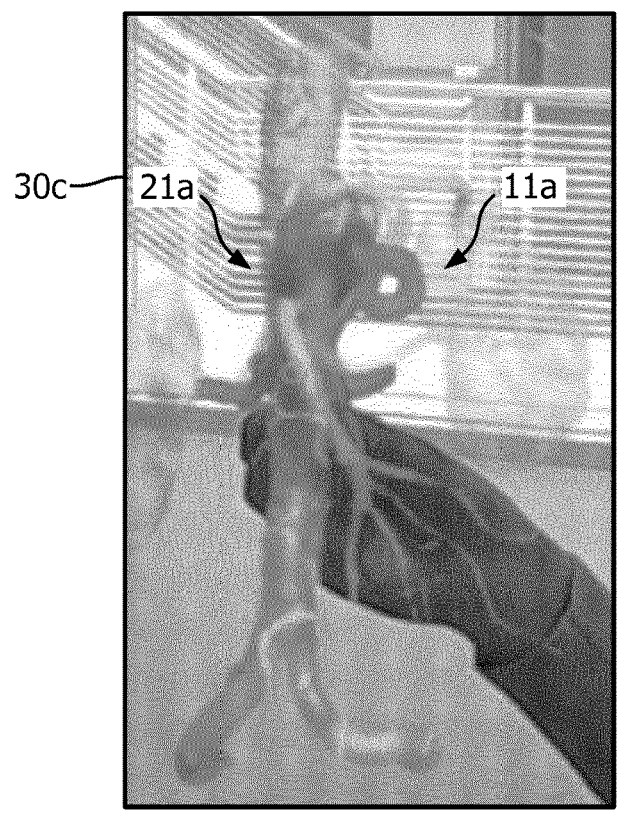
Figure 7C:
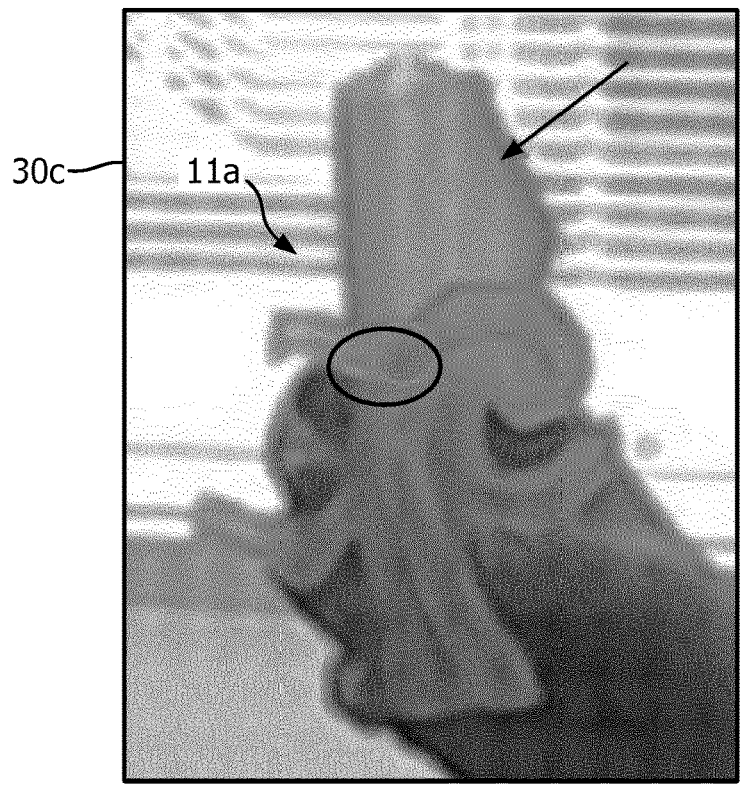
Figure 8:
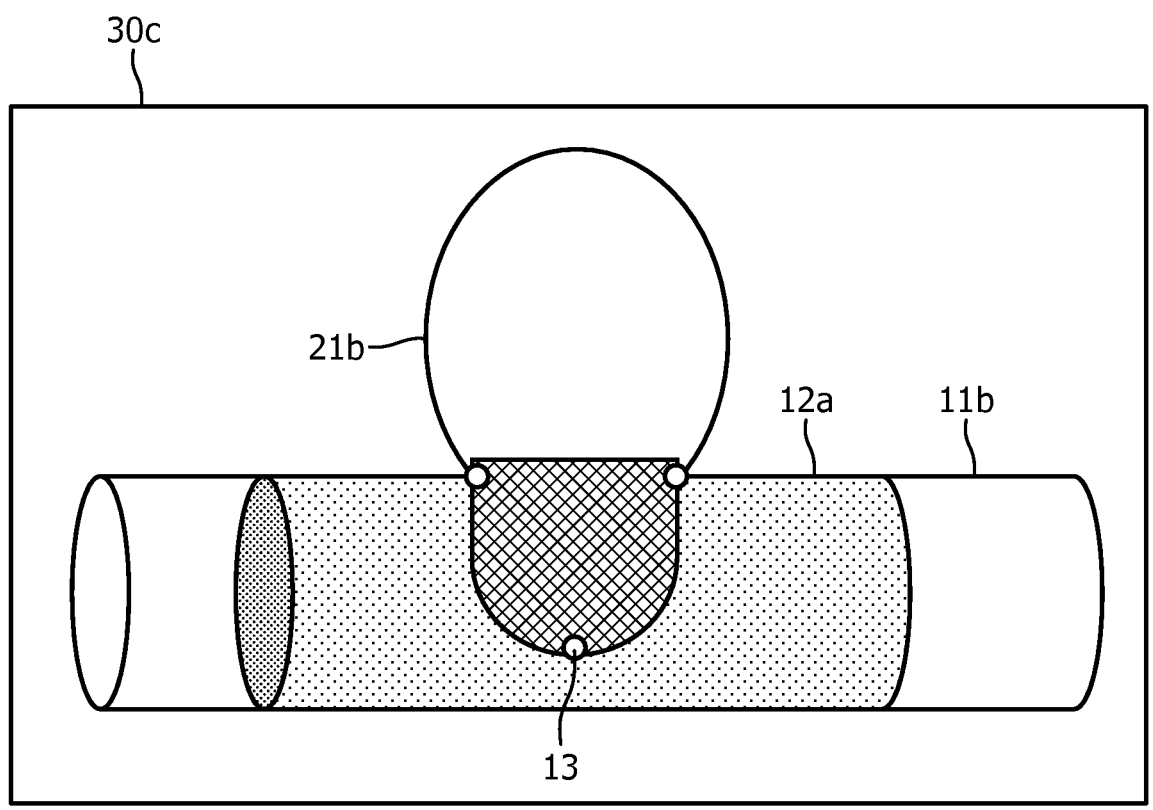
FIG. 8 illustrates an exemplary virtual augmentation of a neurovascular stenting of an aneurysm in accordance with the inventive principles of the present disclosure.

To facilitate an understanding of the present disclosure, the following description of FIGS. 6-8 provides exemplary virtual augmentations of a physical anatomical model 11. From this description, those having ordinary skill in the art will appreciate how to apply the inventive principles of the present disclosure to making and using numerous and varied virtual augmentations of a physical anatomical model 11 in accordance with the inventive principles of the present disclosure.

For a first example, a patient has an abdominal aneurysm, as visualized from a pre-operative CT scan. The anatomy of interest (the abdominal aorta) is segmented from the CT image and a region is 3D printed to form a physical anatomical model 1 la of the aneurysm as shown in FIG. 6. Note only the region around the aneurysm is printed as shown FIG. 6.

During a planning for the procedure, the physicians need to assess how calcified and tortuous the vessels are to plan their approach to the aneurysm. To this end, the physicians view those vessels as an augmented visualization physical anatomical model 11a via a mixed reality device 30c of the present disclosure as shown in FIGS. 7A and 7B (e.g., a Microsoft Hololens mixed reality display incorporating or linked to a mixed reality controller of the present disclosure).

Referring to FIGS. 7A and 7B, mixed reality device 30c detects the physical 3D anatomical model 11a and then overlays a virtual anatomical model 21a (e.g., a hologram) in the correct location (alternatively this could be done with a special marker embedded into the physical anatomical model 11a). A displayed pose of the virtual anatomical model 21a follows the physical anatomical model 11a as physical anatomical model 11a is manipulated by the user (rotated, translated, pivoted, etc.). The physical anatomical model 11a becomes a type of joystick for the user to interact with virtual elements of the virtual anatomical model 21a.

Prior to and during the procedure, a physician may make annotations and place targets on the anatomy. That information can be captured and overlayed virtually onto the virtual anatomical model 21a as symbolically shown by a red arrow and a green circle in FIG. 7C. Intraoperative information (such as x-ray images, ultrasound images, device position from navigation such as EM tracking) may similarly be overlayed in the appropriate context.

Furthermore, the same physical anatomical model 11a may be held by another person in a different place in a hospital and the virtual anatomical model 21a may be shown to them, such as, for example, a vascular surgeon consulting from a different location in the hospital, a student sitting in a classroom, or the patient's family sitting in the waiting room).

Alternative, to FIGS. 7A-7C being displayed in a physical space as shown, physical anatomical model 11a and virtual anatomical model 21a may be displayed in a virtual space. For example, the virtual space may illustrate a virtual patient within a virtual operating room with mixed interaction between the models occurring within the virtual patient.

For a second example, in a neurovascular stenting of aneurisms, often a stent with mesh is used to block the opening of the aneurism to reduce the blood flow in the aneurism. If the mesh covers all the stent then there might be other vessels that might get blocked and cause unintentional flow blockages. This is avoided by customizing the stent by sowing the mesh only on part of the stent which is placed over the neck of the aneurism. Referring to FIG. 8, this can be achieved by overlying a virtual image 21*b* of the aneurism over the stent 12*a* enabling the sowing 13 of the mesh only on the part of the stent 21*a* covering the aneurism neck.

Referring to FIGS. 1-8, those having ordinary skill in the art of the present disclosure will appreciate numerous benefits of the present disclosure including, but not limited to, a utilization of a mixed reality interaction between a physical anatomical model and a virtual anatomical model for purposes of path planning, tool guidance, surgical training and patient consultation.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

In one embodiment, a mixed reality controller of the present disclosure may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware.

Having described preferred and exemplary embodiments of novel and inventive virtual augmentation of anatomical models for path planning, tool guidance, surgical training and patient consultation (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A mixed reality device, comprising:
a physical anatomical model of a patient anatomy configured to be manipulated by a user within a physical space;
a mixed reality display configured to visualize an overlay of a virtual augmentation of the physical anatomical model on the physical anatomical model; and
a mixed reality controller configured to control a visualization, by the mixed reality display, of the virtual augmentation on the physical anatomical model including a mixed reality interaction between the physical anatomical model and a virtual anatomical model based on spatial registration between the physical anatomical model within the physical space and the virtual anatomical model within a virtual space,
wherein the physical anatomical model is configured to be operated as an anatomical joystick, such that as the user operates the physical anatomical model to change pose of the physical anatomical model, the mixed reality controller is configured to change the visualization of the overlay of the virtual augmentation on the physical anatomical model to follow the changed pose of the physical anatomical model.

2. The mixed reality device of claim 1, wherein the mixed reality interaction between the physical anatomical model and the virtual anatomical model includes a virtual interactive overlay of the virtual anatomical model onto the physical anatomical model.

3. The mixed reality device of claim 1, wherein the virtual augmentation of the physical anatomical model of the patient anatomy further includes a virtual annotation of at least one of the physical anatomical model and the virtual anatomical model.

4. The mixed reality device of claim 1, wherein the virtual augmentation of the physical anatomical model of the patient anatomy further includes a mixed reality interaction between a physical medical tool and the virtual anatomical model.

5. The mixed reality device of claim 1, wherein the virtual augmentation of the physical anatomical model of the patient anatomy further includes a mixed reality interaction between the physical anatomical model and a virtual medical tool.

6. The mixed reality device of claim 1, wherein the virtual augmentation of the physical anatomical model of the patient anatomy further includes a mixed reality interaction between a physical medical tool and a virtual medical tool.

7. The mixed reality device of claim 1, wherein the mixed reality controller is structurally configured to control the visualization by the mixed reality display of the virtual augmentation of the physical anatomical model within the physical space.

8. The mixed reality device of claim 1, wherein the mixed reality controller is structurally configured to control the visualization by the mixed reality display of the virtual augmentation of the physical anatomical model within the virtual space.

9. The mixed reality device of claim 1, wherein the mixed reality controller comprises:
a mixed reality registration processor configured to control the spatial registration between the physical anatomical model within the physical space and the virtual anatomical model within the virtual space; and
a mixed reality interaction processor configured to control the mixed reality interaction between the physical anatomical model and the virtual anatomical model based on the spatial registration between the physical anatomical model within the physical space and the virtual anatomical model within the virtual space.

10. The mixed reality device of claim 9,
wherein the mixed reality interaction processor is further configured to control a virtual annotation of at least one of the physical anatomical model and the virtual anatomical model.

11. The mixed reality device of claim 9,
wherein the mixed reality registration processor is further configured to control a spatial registration between a physical medical tool within the physical space and the virtual anatomical model within the virtual space; and
wherein the mixed reality interaction processor is further configured to control a mixed reality interaction between the physical medical tool and the virtual anatomical model based on the spatial registration between the physical medical tool within the physical space and the virtual anatomical model within the virtual space.

12. The mixed reality device of claim 9,
wherein the mixed reality registration processor is further configured to control a spatial registration between the physical anatomical model within the physical space and a virtual medical tool within the virtual space; and
wherein the mixed reality interaction processor is further configured to control a mixed reality interaction between the physical anatomical model and the virtual medical tool based on the spatial registration between the physical anatomical model within the physical space and the virtual medical tool within the virtual space.

13. The mixed reality device of claim 9,
wherein the mixed reality registration processor is further configured to control a spatial registration between a physical medical tool within the physical space and a virtual medical tool within the virtual space; and
wherein the mixed reality interaction processor is further configured to control a mixed reality interaction between the physical medical tool and the virtual medical tool based on the spatial registration between the physical medical tool within the physical space and the virtual medical tool within the virtual space.

14. The mixed reality device of claim 9,
wherein the mixed reality interaction processor is further configured to control the visualization of the mixed reality interaction between the physical anatomical model and the virtual anatomical model within one of the physical space or the virtual space.

15. A mixed reality method, comprising:
controlling a spatial registration between a physical anatomical model within a physical space and a virtual anatomical model within a virtual space;
receiving data of a user operating the physical anatomical model as an anatomical joystick to manipulate visualization of an overlay of a virtual augmentation of the physical anatomical model on the physical anatomical model; and
controlling a visualization of a mixed reality interaction between the physical anatomical model and the virtual anatomical model, including the visualization of the overlay of the virtual augmentation on the physical anatomical model, based on (i) the spatial registration between the physical anatomical model within the physical space and the virtual anatomical model within the virtual space and (ii) the data of the user operating the physical anatomical model as an anatomical joystick,
wherein as the user operates the physical anatomical model as an anatomical joystick to change pose of the physical anatomical model, the visualization of the overlay of the virtual augmentation on the physical anatomical model is changed to follow the changed pose of the physical anatomical model.

16. The mixed reality method of claim 15, further comprising:
controlling a virtual annotation of at least one of the physical anatomical model and the virtual anatomical model.

17. The mixed reality method of claim 15, further comprising:
controlling a spatial registration between a physical medical tool within the physical space and the virtual anatomical model within the virtual space; and
controlling a visualization of a mixed reality interaction between the physical medical tool and the virtual anatomical model based on the spatial registration between the physical medical tool within the physical space and the virtual anatomical model within the virtual space.

18. The mixed reality method of claim 15, further comprising:
controlling a spatial registration between the physical anatomical model within the physical space and a virtual medical tool within the virtual space; and
controlling a visualization of a mixed reality interaction between the physical anatomical model and the virtual medical tool based on the spatial registration between the physical anatomical model within the physical space and the virtual medical tool within the virtual space.

19. The mixed reality method of claim 15, further comprising:
controlling a spatial registration between a physical medical tool within the physical space and a virtual medical tool within the virtual space; and
controlling a visualization of a mixed reality interaction between the physical medical tool and the virtual medical tool based on the spatial registration between the physical medical tool within the physical space and the virtual medical tool within the virtual space.

* * * * *